United States Patent [19]

Ishii et al.

[11] Patent Number: 5,474,895
[45] Date of Patent: Dec. 12, 1995

[54] NON-ISOTOPIC DETECTION OF NUCLEIC ACIDS USING A POLYSTYRENE SUPPORT-BASED SANDWICH HYBRIDIZATION ASSAY AND COMPOSITIONS USEFUL THEREFOR

[75] Inventors: Jennifer K. Ishii; Soumitra Ghosh, both of San Diego, Calif.

[73] Assignee: Siska Diagnostics Inc., La Jolla, Calif.

[21] Appl. No.: 50,441

[22] PCT Filed: Nov. 14, 1991

[86] PCT No.: PCT/US91/08523

§ 371 Date: May 13, 1993

§ 102(e) Date: May 13, 1993

[87] PCT Pub. No.: WO92/08808

PCT Pub. Date: May 29, 1992

Related U.S. Application Data

[63] Continuation-in-part of Ser. No. 613,174, Nov. 14, 1990, abandoned.

[51] Int. Cl.⁶ ............................. C12Q 1/68; C12N 15/11
[52] U.S. Cl. ................. 435/6; 536/24.3; 536/24.31; 536/25.32; 435/91.2; 435/91.21
[58] Field of Search .................... 435/6, 91.2, 91.21; 536/24.3, 24.31, 25.32

[56] References Cited

U.S. PATENT DOCUMENTS

| | | | |
|---|---|---|---|
| 4,302,204 | 11/1981 | Wahl et al. | 23/230.3 |
| 4,358,535 | 11/1982 | Falkow et al. | 435/5 |
| 4,419,444 | 12/1983 | Quash | 435/7.2 |
| 4,469,796 | 9/1984 | Axén et al. | 436/518 |
| 4,486,539 | 12/1984 | Ranki et al. | 436/504 |
| 4,563,419 | 1/1986 | Ranki et al. | 435/6 |
| 4,581,333 | 4/1986 | Kourilsky | 435/6 |
| 4,683,195 | 7/1987 | Mullis et al. | 435/6 |
| 4,683,202 | 7/1987 | Mullis | 435/91.2 |
| 4,775,619 | 10/1988 | Urdea | 435/6 |
| 4,806,546 | 2/1989 | Carrico et al. | 536/25.3 |
| 4,806,631 | 2/1989 | Carrico et al. | 536/25.3 |
| 4,820,630 | 4/1989 | Taub | 435/5 |
| 4,833,251 | 5/1989 | Musso et al. | 548/303 |
| 5,082,780 | 1/1992 | Warren et al. | 435/191 |
| 5,232,829 | 8/1993 | Longiaru et al. | 435/6 |
| 5,237,016 | 8/1993 | Ghosh et al. | 525/329.4 |

FOREIGN PATENT DOCUMENTS

| | | |
|---|---|---|
| 0296557 | 12/1988 | European Pat. Off. |
| 0304934 | 3/1989 | European Pat. Off. |
| 0361768 | 4/1990 | European Pat. Off. |
| 0373960 | 6/1990 | European Pat. Off. |
| WO88/01302 | 2/1988 | WIPO ............ C12Q 1/68 |
| 8810315 | 12/1988 | WIPO |
| 8902932 | 4/1989 | WIPO |
| 8906701 | 7/1989 | WIPO |
| 9007582 | 7/1990 | WIPO |

OTHER PUBLICATIONS

Ghosh et al. (1989), Analyt. Biochem. 178: 43–51.
Bronstein et al. (1989), Analyt. Biochem. 180: 95–98.
Alves, et al., "Hybridization detection of single nucleotide changes with enzyme labeled oligonucleotides," *Nucleic Acids Res.* 16(17):8722 (1988).
Amann, et al., "Identification of individual prokaryotic cells by using enzyme–labeled, rRNA–targeted oligonucleotide probes,"*Appl. Environ. Microbiol.* 58(9):3007–3011 (1992).
Berkowitz, et al., "The inactivation of horseradish peroxidase by a polystyrene surface," *J. Immunol. Methods* 47(1):121–124 (1981).
Bio–Rad Laboratories Catalog 1981, "Affinity Chromatography," pp. 39–50.
Bunemann, et al., "Immobilization of denatured DNA to macropourous supports: I. Efficiency of different coupling procedures," *Nucl. Acids Res.* 10(22):7163 (1982).
Bunemann, et al., "Immobilization of denatured DNA to macropourous supports: II. Steric and kinetic parameters of heterogenous hybridization reactions," *Nucl. Acids Res.* 10(22):7181–7196 (1982).
Cuatrecasas, Pedro, "Protein purification by affinity chromatography," *J. Biol. Chem.* 245:3059–3066 (1970).
Davis, et al., "Detection of HIV–1 in AIDS patients using amplification–mediated hybridization analyses: Reproducibility and quantitative limitations," *J. Infect. Dis.* 162:13–20 (1990).
Duncan, et al., "Anew reagent which may be used to introduce sulfhydryl groups into proteins, and its use in the preparation of conjugates for immunoassay," *Anal. Biochem.* 132:68–73 (1983).
Fahy, et al., "Design and synthesis of polyacrylamide–based oligonucleotide supports for use in nucleic acid diagnostics," *Nucleic Acids Res.* 21(8):1819–26 (1993).
Fowler et al., "Labeling of oligonucleotides with horseradish peroxidase and detection using enhanced chemiluminescence," *Technique*2(5):261–267 (1990).
Gingeras, et al., "Use of self–sustained sequence replication amplification reaction to analyze and detect mutations in zidovudine–resistant human immunodeficiency virus," *J. Infectious Disease* 164:1066 (1991).
*Nucleic Acid Hybridisation*, Hames & Higgins (Eds.), IRL Press, Washington, D.C. (1985). Table of Contents provided.
Inman, John, "Covalent linkage of functional groups, ligands, and proteins to polyacrylamide beads," *Methods in Enzymology* 34(part B):30–39 (1974).
Ishii, et al., "Bead–Based Sandwich Hybridization Charac (List continued on next page.)

Primary Examiner—Mindy B. Fleisher
Assistant Examiner—Philip W. Carter
Attorney, Agent, or Firm—Stephanie L. Seidman; Brown Martin Haller & McClain

[57] ABSTRACT

Methods for the detection of nucleic acid using sandwich hybridization are provided. The target nucleic acids are captured by hybridization with oligonucleotides covalently attached to polystyrene solid supports to form complexes which are then hybridized to detection oligonucleotides to facilitate the analysis of the target nucleic acid sequences.

22 Claims, 1 Drawing Sheet

OTHER PUBLICATIONS teristics of Oligonucleotide–Alkaline Phosphatase Conjugates and Their Potential for Quantitating Target RNA Sequences," *Bioconj. Chem.* 4(1):34–41 (1993).

Kwoh, et al., "Transcription–based amplification system and detection of amplified human immunodeficiency virus type 1 with a bead–based sandwich hybridization format," *Proc. Natl. Acad. Sci.* 86:1173 (1989).

Langdale and Malcolm, "A rapid method of gene detection using DNA bound to Sephacryl," *Gene* 36:201–210 (1985).

Medon, et al., "Identification of enterotoxigenic *Escherichi coli* isolates with enzyme–labeled synthetic oligonucleotide probes," *J. Clin. Microbiol.* 26(10):2173–76 (1988).

Musso, et al., "Synthesis of N–[6–(ethlyenedioxy)hexyl] biotinamide: a biotinyl aldehyde precursor for labelling hydrazine–modified biomolecues," *Bioconj. Chem.* 3:88–90 (1992).

Pongs and Lanka, "Synthesis of a chemically reactive analog of the initiation codon its reaction with ribosomes of *Escherichia coli,*" *Hoppe Seyler's Z. Physiol. Chem.* 356:449–458 (1975).

Ratner, et al., "Complete nucleotide sequence of the AIDS virus, HTLV–II," *Nature* 313:277–284 (1985).

Urdea, et al., "A comparison of non–radioiostopic hybridization assay methods using fluorescent, chemiluminescent and enzyme labeled synthetic oliodeoxyribonucleotide probes," *Nucleic Acids Res.* 16(11):4937–56 (1988).

Yamamoto, et al., "Enzyme–labeled oligonucleotide probes for detection of the genes for thermostable direct hemolysin (TDH) and TDH–related hemolysin (TRH) of *Vibrio parahaemolyticus,*" *Can. J. Microbiol.* 38(5):410–416 (1992).

Yoh, et al., "Development of an enzyme–labeled oligonucleotide probe for the cholera toxin gene," *J. Clin. Microbiol.* 31(5):1312–1314 (1993).

Goodchild, *Bioconj. Chem.* 1:165 (1990).

Ghosh, et al. *Bioconj. Chem.* 1:71 (1990).

Ghosh, et al., *Nucl. Acids Res.* 15:5353.

Urdea, et al., *Gene* 61:253.

Lund, et al., *Nucl. Acids Res.* 16:10861.

Syvanen, et al., *Nucl. Acids Res.* 16:11327.

Voss, et al., *Bioch. Soc. Trans.* 624th Mtg. Dublin.

Blanks, et al., *Nucl. Acids Res.* 16:10283.

Beck, et al., *Nucl. Acids Res.* 17:5115.

Kremsky, et al., *Nucl. Acids Res.* 15:2891 (1987).

Li, et al., *Nucl. Acids Res.* 15:5275 (1987).

NON-ISOTOPIC DETECTION OF NUCLEIC ACIDS USING A POLYSTYRENE SUPPORT-BASED SANDWICH HYBRIDIZATION ASSAY AND COMPOSITIONS USEFUL THEREFOR

RELATED APPLICATIONS

This application is a continuation-in-part of U.S. patent application Ser. No. 07/613,174, to Ishii et al., filed Nov. 14, 1990, "NON-ISOTOPIC DETECTION OF NUCLEIC ACID SEQUENCES IN A POLYSTYRENE SUPPORT-BASED SANDWICH HYBRIDIZATION ASSAY AND COMPOSITIONS USEFUL THEREFOR", now abandoned. The subject matter of U.S. patent application Ser. No. 07/613,174 is incorporated herein in its entirety by reference thereto.

FIELD OF THE INVENTION

The present invention relates to means for the detection of nucleic acid sequences. In particular, the invention relates to bead-based hybridization assay systems that are useful for the capture and detection of nucleic acids, including RNA and single-stranded DNA targets. In another aspect, this invention relates to kits and compositions for practicing the bead-based hybridization assays.

BACKGROUND OF THE INVENTION

It is often desirable to detect very small amounts of nucleic acids, such as samples obtained from biological samples. According to one common approach, nucleic acids, target nucleic acids, are extracted from the sample and are hybridized to an oligonucleotide to form a detectable complex. In order to obtain a detectable signal that can be correlated with the amount of the target, either the target nucleic acid or the oligonucleotide is associated with a signal generating reporter element, such as a radioactive atom, a fluorescent or chromogenic molecule, or an enzyme which is capable of converting a substrate into a product which can be detected and measured. The signal generated, directly or indirectly, by a properly hybridized nucleic acid is detected and measured by methods known in the art.

Many of the commonly used techniques of molecular biology, including fractionation and identification of specific sequences of nucleotide bases, involve the immobilization of target nucleic acid sequences on solid supports. For example, target nucleic acid sequences have been immobilized on nylon or nitrocellulose membranes, then detected with an oligonucleotide having a radioactive label attached thereto. Alternatively, so-called "sandwich" hybridization systems may be employed, using a capture oligonucleotide, which includes a sequence of nucleotide bases homologous to or complementary to the target and which is covalently attached to, or non-covalently associated with, a solid support, and using a detection oligonucleotide, which is an oligonucleotide covalently attached to, or non-covalently associated with, a reporter group, such as a radioactive label or a detection enzyme, and that has a sufficient complementarity with the target nucleic acid sequence in a region that is different from that portion of the target nucleic acid sequence which hybridizes to the capture oligonucleotide under conditions such that a dual hybridization occurs with the target sequence. The capture oligonucleotide, target nucleic acid and detection oligonucleotide form a sandwich complex by hybridization of the target with both the capture and detection oligonucleotide.

The solid support may be in the form of beads in which case the assay is referred to as a "bead-based sandwich hybridization system" (herein referred to as a BBSHS). A BBSHS is described, for example, in European Patent Application No. 276,302. According to this method, in a first step, the target nucleic acid and an oligonucleotide probe used for its detection, which is complementary to a first region of the target, are hybridized. The complex thus formed is then captured by a second oligonucleotide that is complementary to a different region of the target. In addition, the capture oligonucleotide is preferably end-attached to a solid support. The amount of the detection oligonucleotide associated with the solid support after these hybridization steps is directly related to the amount of the target nucleic acid captured. In this way, the BBSHS can be used to determine the amount of a specific single-stranded nucleic acid in a sample. In this and similar assays, radioactively (e.g., $^{32}P$) labeled cloned DNAs or synthetic oligonucleotides are most commonly employed because of the high sensitivity which can be obtained with such labels. $^{32}P$-labeled oligonucleotide probes used in conjunction with SEPHACRYL™ or TRISACRYL™ (Sepracor Inc.) beads in BBSHS experiments provide about 10:1 or better signal to noise ratios with target sequences present in about 0.5 mole amounts.

In practice, because of the inconveniences associated with handling, storage and disposal of radioisotopes, non-radioisotopic reporter systems are often used. Successful application of a non-radioisotopic reporter system requires a detection system which exhibits high sensitivities and low background properties when used in conjunction with the reporter system on a given solid support. The SEPHACRYL™ bead supports have been previously shown to possess serious limitations when used in conjunction with non-radioisotopic (e.g., colorimetric) detection systems (see, for example, International Application No. PCT/US90/00089). For example, the colorimetric signal from enzyme-oligonucleotide conjugates in sandwich formats and direct capture experiments on Sephacryl beads are compromised by undesirable background signal level, thereby giving low signal to noise ratios.

Non-specific background (in the presence of target nucleic acid) can be a result of:
1) hybridization of the detection and capture oligonucleotides to non-exact sequences of the target nucleic acid;
2) direct hybridization of the detection oligonucleotide to the capture oligonucleotide; or
3) non-specific attachment of the detection oligonucleotide to the bead support or walls of the reaction vessel.

While the first two of these possible cause as can be minimized by sufficiently stringent solution hybridization, capture and wash conditions, non-specific binding properties are poorly understood.

As described in International Application No. PCT/US90/00089, TRISACRYL™ support has been shown to be a more selective support than SEPHACRYL™ for use in bead-based sandwich hybridization assays. When Trisacryl is used, however, in a bead-based hybridization assay with non-isotopic detection, e.g., using alkaline phosphatase as the reporter enzyme and a chemiluminescent (herein abbreviated as CL) substrate, the sensitivity of the Trisacryl-based assay is only about one femtomole (see, e.g., the Examples provided herein).

It would be desirable to find solid supports that have better binding properties, including reduced levels of non-specific attachment of the oligonucleotides used for detection of the target nucleic acids and increased capture potential of the immobilized probe, especially when used in conjunction with non-radioisotopic detection systems.

Desirable properties of solid supports contemplated for use in hybridization detection of nucleic acids include: hydrophilicity; ease of handling, including the ability to form stable suspensions thereby obviating the need for agitation of the assay mixture, as well as compatibility with standard recovery techniques, such as filtration or centrifugation; suitable functional groups on the surface of the solid support; and low non-specific binding with the detection oligonucleotides.

Typical solid supports employed for direct capture and sandwich hybridizations are, for example, nitrocellulose or nylon membranes, activated agarose supports and diazotized cellulose supports. These supports, however, do not meet all of the above criteria. For example, the bonds between these supports and the capture oligonucleotides-are either not covalent, thereby allowing a certain release of the oligonucleotides from the support, or the supports have other shortcomings. For example, N-hydroxysuccinimide or cyanogen bromide activated polysaccharide affinity supports have a serious drawback in the leakage of ligands, which interferes with affinity purification. If the free ligand that leaks from the support is more effective as a binder than the insolubilized ligand, the free ligand binds the target macromolecule essentially irreversibly, and prevents affinity adsorption to the column. Further, cyanogen bromide activation of polysaccharide supports leads to the formation of N-substituted isoureas on the surface of the matrix. These confer undesirable ion exchange properties to the support, which become problematic in affinity chromatography, when analytes (such as nucleic acids) are present in very minute concentrations.

Therefore, solid supports with cross-linked, polymeric matrix structures, to which capture oligonucleotides can be covalently and stably end-attached, and which meet the above criteria, are continually being sought for improved hybridization assay systems.

Therefore, it is an object of this invention to provide solid supports with cross-linked, polymeric matrix structures, to which capture oligonucleotides can be covalently and stably end-attached for use in such sandwich hybridization systems and assays.

It is also an object to provide sandwich hybridization assay systems and assays that are sufficiently sensitive to detect very low concentrations of a target nucleic acid and that may be sufficiently sensitive to distinguish between target nucleotides that differ in sequence in only a few nucleotides.

SUMMARY OF THE INVENTION

Highly sensitive assays for detecting as little as $10^{-17}$ moles of nucleic acid molecules are provided. In particular, sandwich hybridization systems using polystyrene solid supports and non-radioactive detection means are provided. Analytical systems and compositions for practicing the methods are also provided. Further, the assays provide a means for detecting very low concentrations of nucleic acid molecules in solution without requiring the use of radioactive compounds.

Even though Trisacryl-supported sandwich hybridization systems provide excellent sensitivity when used with radioactively labeled detection oligonucleotides (indeed, Trisacryl-supported systems are superior to polystyrene-supported systems under such conditions), polystyrene-supported sandwich hybridization systems provide unexpectedly superior sensitivity when used with non-radioactively labeled detection oligonucleotides. TRISACRYL™ is a hydrophilic crosslinked polyacrylamide resin in which the amide hydrogens are substituted with 2-hydroxymethyl-1, 3-propane diol groups.

The above aspects and all associated methods and means for accomplishing such are also provided. For example, methods for preparation and purification of the detection and capture oligonucleotides, including synthesis or isolation from a natural source via restriction cleavage and subsequent purification; methods for the preparation of oligonucleotide-reporter molecule, such as enzymes capable of generating a chemiluminescent signal when contacted with a suitable substrate, complexes for use in hybridization with the target nucleic acids; hybridization techniques for hybridizing the target nucleic acid to the detection (and capture) oligonucleotide(s); and so forth are provided herein.

In particular, methods for the detection of target nucleic acids in which the target nucleic acid sequence is hybridized to a first portion of a detection oligonucleotide, which has a reporter enzyme covalently bound thereto, to form a complex, which is then hybridized to a polystyrene solid support-bound capture oligonucleotide which has substantial complementarity to a second portion of the target nucleic acid sequence to produce a polystyrene support-bound {capture oligonucleotide-target nucleic acid-detection oligonucleotide} sandwich complex. The sandwich complex is washed under conditions sufficient to remove substantially all unhybridized detection oligonucleotide therefrom and is then reacted with a suitable substrate under conditions such that reporter enzyme in the sandwich complex promotes the conversion of the substrate into a detectable product and/or signal indicative of the reaction of substrate with reporter enzyme, whereby the target nucleic acid is detected or its concentration is determined by measuring the product and/or signal.

In accordance with another embodiment, the target nucleic acid is simultaneously contacted with the detection oligonucleotide (as defined above) and a solid support-bound capture oligonucleotide to produce a sandwich complex, which is washed under conditions sufficient to remove substantially all unhybridized detection oligonucleotide therefrom. The sandwich complex is then reacted with a suitable substrate under conditions such that the reporter enzyme catalyzes the conversion of the substrate to produce a detectable product and/or signal indicative of the reaction of substrate with reporter enzyme. The target nucleic acid is then detected or its concentration determined by measuring the signal and/or product produced when said substrate is reacted with the reporter enzyme.

In certain embodiments, in which the concentration of target nucleic acid is too low for the hybridization reaction to occur in a reasonable time or is too low to be detectable, the concentration of target nucleic acid is amplified prior to the first hybridization. In addition, since the hybridization reaction with the detection oligonucleotide or the detection and capture oligonucleotides requires single-stranded target molecules, if the target nucleic acids are not single-stranded, such as DNA or double-stranded RNA, they are rendered single-stranded prior to hybridization.

In accordance with other embodiments, there is provided a solid support-based sandwich hybridization assay system or kit for the detection of single-stranded, target nucleic acids. The system or kit includes a solid support-bound capture oligonucleotide that is covalently attached to a polystyrene support and that includes a sequence of nucleotide bases that has substantial complementarity with a first portion of a target nucleic acid sequence; a detection oligonucleotide that includes a sequence of nucleotide bases that has substantial com-complementarity with a second portion, which differs from the first portion, of a target nucleic acid sequence and that has a reporter enzyme covalently bound thereto; and a substrate for the reporter enzyme, which catalyzes a reaction that can be quantified by chemiluminescent, colorimetric, potentiometric, or fluorescent means.

In accordance with still another embodiment, a composition of matter containing a polystyrene support-bound {capture oligonucleotide-target nucleic acid-detection oligonucleotide} sandwich complex is provided.

DETAILED DESCRIPTION OF THE INVENTION

Figure 1:
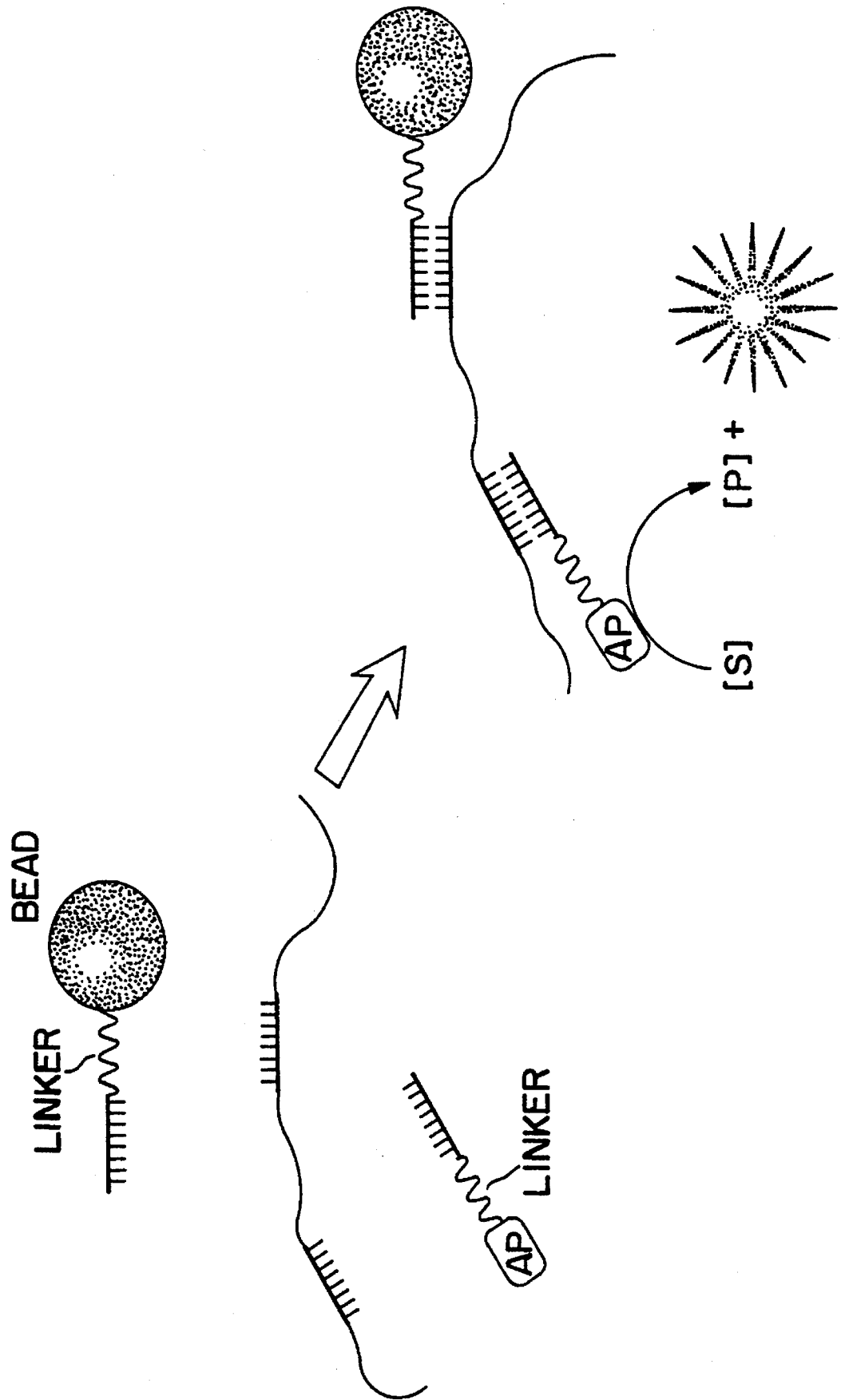
FIG. 1 illustrates the components of a sandwich hybridization complex, and the inter-relationships among the various components thereof.

Definitions:

Unless defined otherwise, all technical and scientific terms used herein have the same meaning as is commonly understood by one of skill in the art. All publications mentioned herein are incorporated by reference thereto. All U.S. patents mentioned herein are incorporated in their entirety by reference thereto.

As used herein, oligonucleotide refers to nucleic acids including both single stranded RNA and DNA molecules that may be synthesized, may be isolated from a natural source, or may be produced by standard molecular biological techniques.

As used herein, the term "PCR" refers to the transcription amplification system disclosed in U.S. Pat. Nos. 4,683,195 and 4,683,202, the contents of which are hereby incorporated by reference herein in their entirety.

The term "TAS" as used herein refers to the transcription amplification system disclosed in PCT International Publication No. WO 88/10315. This method involves the use of multiple reaction cycles employing reverse transcriptase, T7 RNA polymerase and suitably designed oligonucleotide primers to prime the synthesis of RNA transcripts via cDNA intermediates.

The term "3SR" as used herein refers to the transcription amplification system disclosed in European Patent Application No. 373,960. This method involves employing a combination of enzymes having reverse transcriptase activity, T7 RNA polymerase activity, and RNaseH activity, plus suitably designed oligonucleotide primers to prime the synthesis of RNA transcripts via cDNA intermediates.

As employed herein, the term "target nucleic acid" refers to the portion of the analytical sample which is to be measured. Target nucleic acids include, but are not limited to, nucleic acids that are derived from sources which are implicated in the propagation of infectious diseases (e.g., vital or bacterial sources), nucleic acids which are produced by recombinant means, nucleic acid sequences indicative of the presence of genetic abnormalities, and other biologically important nucleic acids.

As used herein, when describing the process of immobilizing oligonucleotides on solid supports, the terms "attachment", "coupling" "tether", "binding" and "immobilization" are used interchangeably and refer to covalent linkage of oligonucleotides to the solid supports.

The term "detection oligonucleotide" or grammatical variations thereof as used throughout the specification and the claims refers to an oligonucleotide sequence (RNA or single-stranded DNA; wherein said oligonucleotide is isolated from a natural source, synthetically produced, or is a product of standard molecular biological techniques) covalently bound to a reporter molecule. The oligonucleotide sequence of the detection oligonucleotide has sufficient homology or complementarity with a target nucleic acid sequence such that, under suitable conditions, it is capable of hybridizing with said target nucleic acid sequence.

As used herein, sensitivity refers to the lowest concentration of target nucleic acid that can be detected. Specificity refers to the ability of the assay to discriminate among target nucleic acids.

As used herein, a stable hybrid, is a hybrid that includes a sufficient number of complementary nucleotides to render the resulting hybrids detectable. The formation of stable hybrids is a function of the extent of complementarity between the hybridizing nucleic acids and also the sequence of the nucleotides that form the hybrids. Generally ten or more substantially matching contiguous nucleotide bases are-sufficient to form a stable hybrid. One of skill in the art recognizes, however, that stability is a function of numerous parameters, including the particularly matched and mismatched nucleotides, the length of the mismatches and the overall length of the hybrid. Substantially matching includes nucleotides that form base pairs and pairs of nucleotide bases that are not sterically prohibited or that destabilize the double stranded helix. One of skill in the art can readily ascertain the minimum number of matching nucleotides that are sufficient for a particular set of capture, detection, and target oligonucleotides. A properly hybridized nucleic acid refers to a hybrid formed between single stranded nucleic acids that include at least one region of substantially matching nucleotides sufficient to form a stable hybrid.

The term "reporter molecule" refers to a molecule, such as an enzyme, which is capable of generating a detectable signal (e.g., by colorimetric, chemiluminescent, fluorescent, or potentiometric means) when contacted with a suitable substrate under appropriate reaction conditions. Exemplary reporter enzymes include alkaline phosphatase, horseradish peroxidase, β-galactosidase, aryl esterase, sulfatase, urease, or the like.

The covalent attachment of the reporter enzyme to the detection oligonucleotide sequence can be accomplished in a variety of ways, as can readily be identified by those of skill in the art. See, for example, Goodchild (1990) *Bioconjugate Chemistry* 1: 165–191, and references cited therein; and Ghosh, et al. (1990) *Bioconjugate Chemistry* 1: 71–76.

Suitable substrates for the reporter enzyme are compounds which are convertible by the reporter enzyme to produce a compound and/or a signal which can be quantified by chemiluminescent, fluorescent, potentiometric or colorimetric means.

Exemplary substrates for use with the above-described enzymes include dioxetane derivatized substrates for alkaline phosphatase, β-galactosidase, aryl esterase, or sulfatase; diacyl hydrazines (e.g., luminol) as a substrate for horseradish peroxidase; urea as a substrate for urease; and the like. Preferred substrates are compounds which, upon reaction with the reporter enzyme, produce a signal which can readily be quantified by chemiluminescent means, including, but not limited to, dioxetane derivatized substrates for alkaline phosphatase, β-galactosidase, aryl esterase, sulfatase, or the like.

The term "capture oligonucleotide", as employed herein, specifically refers to a nucleic acid (RNA or DNA) sequence (isolated from a natural source, synthetically produced, or a product of standard molecular biological techniques) that is covalently attached to a polystyrene solid support, and that has sufficient complementarity with a target nucleic acid sequence (different from that portion of the target nucleic acid sequence which hybridizes to the detection oligonucleotide) such that under suitable conditions it is capable of hybridizing with said target nucleic acid sequence.

As to other aspects of the means and methods used herein, including preparation and purification of oligonucleotides, preparation of oligonucleotide-target nucleic acid adducts, methods for attachment of oligonucleotides to solid supports, hybridization methodologies, detection and measurement of signals generated by properly hybridized nucleic acids, etc., reference is made to standard textbooks of synthetic methods and molecular biology.

See, for example, Maniatie, et al. (1982) *Molecular Cloning: A Laboratory Manual*, Cold Spring Harbor Laboratory, New York, and the various references cited therein; Davis et al. (1986) *Basic Methods in Molecular Biology*, Elsevier Science Publishing, Inc., New York; and Hames, (1985) "*Nucleic Acid Hybridization*", IRL Press. The bead-based hybridization assay system.

Because of the high sensitivity and selectivity of the assays, they are particularly amenable for use in the diagnosis of disease, such as the detection of viruses, such as human immunodeficiency viruses (HIVe), in blood cell samples. For example, in accordance with a particular embodiment, the target nucleic acid sequence is the 3SR amplified HIV-1 (LAV) env region antisense RNA product generated from either of the primer combinations 88-211/88-347 (SEQ ID NO 8/SEQ ID NO 9) or 89-255/90-374 (SEQ ID NO 10/SEQ ID NO 11), The assays require the preparation of detection oligonucleotides, polystyrene bound capture oligonucleotides, and target oligonucleotides. In practicing the assays described herein, target nucleic acid is obtained from a sample, typically a biological sample, such as blood. The target nucleic acid is isolated or purified by standard methods known to those of skill in the art. If the sample or target nucleic acid is available in only minute quantities, it may be amplified. If the target nucleic acid is not single-stranded it must be rendered single-stranded for the hybridization reactions.

The detection oligonucleotides and capture oligonucleotides include regions that are substantially complementary to non-overlapping regions of the target nucleic acid, so that both the detection and capture oligonucleotides can simultaneously hybridize to the target nucleic acid. The oligonucleotides are single-stranded DNA molecules or are derived from double-stranded molecules by melting of the strands using standard methods. The capture oligonucleotide is covalently linked to the polystyrene support and the detection oligonucleotide includes a non-isotopic reporter moiety, such as an enzyme. In preferred embodiments, the linkage between the nucleotide portion of the detection oligonucleotide and the reporter moiety is designed so that hybridization with the target nucleic acid is not sterically or otherwise inhibited. The polystyrene support is formed in any shape, preferably in the shape of beads, and forms a stable suspension in the hybridization reaction mixture.

The detection oligonucleotide is hybridized with the target nucleic acid in solution to form complexes which are then hybridized to the capture oligonucleotide bound to the polystyrene support. Alternatively, the detection and support-bound capture oligonucleotides are simultaneously hybridized with the target nucleic acid. The hybridization reactions are performed under conditions that promote the formation of stable hybrids between complementary regions of the target and detection and capture oligonucleotides, and that minimize non-specific binding or the formation of mismatched hybrids. Such conditions can be empirically determined and it is within the level of skill in the art to select hybridization reaction conditions. The hybridization reactions proceed for a time sufficient to go to completion.

Following hybridization, the beads with bound sandwich complexes are washed under conditions that are sufficiently stringent to remove non-specifically bound or weakly hybridized detection oligonucleotides.. Determination of such conditions is within the level of skill in the art and is a function of the particular target nucleic acid, the desired selectivity and other factors.

A suitable substrate for the reporter moiety, which is typically an enzyme that catalyzes the conversion of the substrate into a product that is directly or indirectly detectable, is mixed with the washed beads. Upon completion of the reaction with substrate the signal is detected. Detected signal can be used to assess the presence of, or concentration of, the target nucleic acid.

Preparation of the components of the bead based hybridization assays.

Target nucleic acids.

Target nucleic acids contemplated for use herein may be of any length. The effects of nucleic acid length on hybridization reactions are well known and selection of suitable conditions for the hybridization reactions are within the level of skill in the art. Typically, target nucleic acids are up to about 2000 nucleotides in length, and are preferably in the range of about 200 up to 600 nucleotides in length. Exemplary target nucleic acids include single-stranded M13 phage or portions thereof and single-stranded M13 that includes heterologous DNA; DNA and RNA viruses; RNA transcript; nucleic acids obtained as the result of 3SR amplification, TAS amplification, PCR amplification, or RNA or DNA extraction. Preferred target nucleic acids are obtained by RNA or DNA extraction or by extraction coupled with one or more amplification methods.

Amplification of the target nucleic acids by 3SR is herein preferred because the methods herein are particularly well-suited for the detection of nucleic acids which are usually present in extremely small amounts that are not generally detectable using standard techniques, and because the product of the 3SR amplification reaction is a single-stranded RNA molecule that is directly amenable for use in sandwich hybridization reactions.

Preparation of detection and capture oligonucleotides.

Oligonucleotides can be synthesized and purified by any method known in the art, including but not limited to, the solid-phase cyanoethyl phosphoramidite method and HPLC purification (Ghosh, etal. (1987) *Nucl. Acids Res.* 15: 5353). Alternatively, they can be isolated from natural sources or produced synthetically or by restriction enzyme cleavage and, if desired, tailored so as to be suitable for the intended use.

Typical detection and capture oligonucleotides are at least about 20 (up to 100 or more) nucleotides in length, with lengths in the range of about 25 up to 35 nucleotides being preferred.

A reporter moiety or molecule, such as an enzyme, is typically covalently linked to the detection oligonucleotide via alkyl or other suitable linkages. In preferred embodiments, the reporter moiety is separated from the oligonucleotide by including a linker of sufficient length to prevent or at least reduce unfavorable interactions between the reporter molecule and the target nucleic acid. By selecting a spacer the signal and sensitivity of the assay can be increased. Selection of the particular spacer size thereof is within the level of skill in the art and is a function of the enzyme moiety, substrate, detection oligonucleotide and target nucleic acid. It has been found that a linker of about 2 to 6 carbons, preferably about 6 carbons increases the signal generated in the embodiments described herein.

Suitable spacers which can be used for the covalent attachment of the reporter enzyme to the detection oligonucleotide sequence include primary alkyldiamines, alkyldiols, alkyl-thiols, phosphates and thiophosphates, and other linkers that have properties which function as described herein. For example, a typical alkyl spacer employed for the covalent attachment of the reporter enzyme to the detection oligonucleotide includes a carbon backbone chain in the range of about 2 up to about 20 carbon atoms; with a preferred carbon backbone chain in the range of about 2 up to about 10 carbon atoms; and most preferred carbon backbone chain in the range of about 5 up to about 10 carbon atoms.

Polystyrene supports.

"Polystyrene supports" contemplated for use in the practice of the present invention are cross-linked polystyrene matrices that are commercially available in a wide range of particle sizes. It is desirable to use particles of such size that they form a stable suspension in the hybridization reaction, thereby obviating the need for agitation of the hybridization mixture during the hybridization reaction, but that are large enough to be separated from the suspension by readily available physical means, such as by filtration, centrifugation, and the like. Additionally, the particles used should not be so large that the surface available for nucleic acid interaction is insufficient for the desired application. Typical particle sizes fall in the range of about 0.1 up to 10 microns; with particle sizes in the range of about 0.5–5 µ being preferred. Particle sizes of about 0.8 µ are presently most preferred as such supports are well suited to each of the above criteria of suspendability and recoverability.

The polystyrene supports preferably contain a sufficient number of functional groups to permit covalent attachment to the polystyrene polymer of a concentration of at least 0.1 nmol of the capture oligonucleotide per gram of polystyrene polymer. Preferably, the concentration of capture oligonucleotide, per gram of polystyrene polymer, falls in the range of about 1 up to 300 nmol/g.

Combinations of functional groups which are useful for the covalent attachment of capture oligonucleotide to the solid support are, for example, selected from among, but not limited to, carboxyl groups and amine groups (which could participate in the formation, for example, of amide bonds), aldehyde groups and hydrazine groups (which could participate in the formation, for example, of hydrazone bonds), epoxide groups and amine groups (which could participate in the formation, for example, of carbon-nitrogen bonds), bromoacetyl groups or maleimide groups and thiol groups (which could participate in the formation, for example, of thioether bonds), and the like. Presently preferred functional groups on the surface of the polymer particles are carboxyl groups.

The preferred reactive functionality for attachment of the capture oligonucleotide to the solid support is an amine group at the terminus of an alkyl linker. The alkylamine linker may be attached to the 5'- or 3'-end of the oligonucleotide sequence, or at the C-5 position of an internal thymidine base of the sequence. The primary amine group of the linker permits end-attachment to a carboxyl-substituted support via dimide-mediated reaction. The preferred position of the amine group is at the 5'-end of the sequence. The preparation of such derivatized oligonucleotides can, for example, be carried out using the Aminolink2reagent (Applied Biosystems, Inc., Foster City, Calif.), which introduces an alkylamine group at the 5'-end via phosphoramidite chemistry.

Representative examples of polystyrene matrices contemplated for use in accordance with the methods described herein, include, but are not limited to, "latex CML" beads, manufactured by Dow Chemical Co. (Midland, Mich.); and distributed by Seradyn (Indianapolis, Ind.) that are further categorized according to particle size. Although the experiments described herein have been conducted primarily with latex CML beads (0.807 µ), other polystyrene supports, including those in which the polymer backbone is substituted with certain functional groups, e.g. the polystyrene is substituted with aldehyde groups, may also be used (see, e.g., Kremsky, et al. (1987) *Nucleic Acids Research*, 15: 2891–2909). See, also, Ghosh and Musso (1987) *Nuleic Acids Research*, 15: 5353–5372 for examples of various coupling chemistries.

The direct capture and background properties of polystyrene bound oligonucleotides have been tested with detection oligonucleotides that are oligonucleotide-alkaline phosphatase conjugates. The background from non-specific binding when employing polystyrene supports was found to be quite low. Furthermore, the sensitivity of the assay when a reporter molecule and a polystyrene support-bound capture oligonucleotide are used is much higher than when such reporter molecules are used with oligonucleotides bound to TRISACRYL™ supports. The greater sensitivity of polystyrene supports was demonstrated in bead-based sandwich hybridization detection of complementary RNA target sequences using oligonucleotide-enzyme conjugates.

Hybridization reaction conditions.

Hybridization of the target nucleic acids to the detection and capture oligonucleotides is conducted under conditions such that stable hybrids form between complementary regions on the target nucleotide and regions on the detection and capture oligonucleotides. The selection of such conditions is within the level of skill in the art and include those in which a low, substantially zero, percentage of mismatched hybrids form. The precise conditions depend, however, on the desired selectivity and sensitivity of the assay. Such conditions include, but are not limited to, the temperature at which the reaction is conducted, the salt concentration of the buffer, the viscosity of the buffer, the respective concentrations of the target nucleic acids and the capture and detection oligonucleotides.

Suitable hybridization buffers and conditions for use in the practice of the present invention can readily be determined by those of skill in the art. For example, in certain embodiments the target nucleic acids are hybridized to the detection oligonucleotide at a temperature in the range of about 25°–55° C. for a time in the range of about 0.1 up to 6 hours in a suitable hybridization buffer; with preferred hybridization temperatures falling in the range of about 42°–50° C.; and preferred hybridization times falling in the range of about 0.5 up to 2 hour and more preferred hybridization times falling in the range of about 1.0 up to 1.5 hours.

The preferred concentrations of the detection oligonucleotide are preferably in the range of about 10 up to 200 fmoles; with preferred detection oligonucleotide concentrations in the range of about 40 up to 80 fmoles; and most preferred detection oligonucleotide concentrations in the range of about 50 up to 70 fmoles.

Typical hybridization conditions for contacting the target nucleic acid-detection oligonucleotide complex with solid support-bound capture oligonucleotide include temperatures in the range of about 25° up to 55° C. for about 0.1 up to 6 hours in a suitable hybridization buffer.

In accordance with embodiments in which the target nucleic acid is simultaneously contacted with a detection oligonucleotide and a solid support-bound capture oligonucleotide, the hybridization reaction is conducted at temperature in the range of about 25° up to 55° C. for about 0.1 up to 6 hours in a suitable hybridization buffer; with preferred hybridization times falling in the range of about 0.5 up to 2 hours; and most preferred hybridization times falling within the range of about 1.0 up to 1.5 hours.

As shown in the examples which follow, and as recognized by those of skill in the art, the efficiency of the hybridization reaction is enhanced by elevated temperatures. Elevated temperatures, however, are detrimental to the stability of the reporter enzyme. Thus, it is desirable to conduct the hybridization reactions at temperatures as high as the reporter enzyme can withstand, without undergoing a substantial loss of enzymatic activity, while also minimizing the time over which the reporter enzyme is subjected to such elevated temperatures. Accordingly, a hybridization temperature of about 50° C. for about 1 hr (total hybridization time— divided into two approximately equal duration hybridization steps when the two-step protocol is used, or as one 1 hour contacting when the one-step protocol is employed) are the presently most preferred hybridization conditions.

Suitable hybridization buffers contemplated for use in the practice of the present invention contain glycerol and a high concentration of salt. An exemplary high salt buffer is 10X SSC which contains: 1.5M sodium chloride, and 0.15M sodium citrate, adjusted to a pH of 7. A typical hybridization buffer contains in the range of about: 2–5X SSC, 0.1–0.5% SDS, 0–0.05 µg/µl of carrier DNA (calf thymus), 0–5X PVP/Ficoll, and 0–2.5% glycerol, in a total reaction volume of 25–100 µl. The PVP/Ficoll can be prepared by appropriate dilution of a 10) PVP/Ficoll preparation which is a mixture of 5 grams polyvinyl pyrrolidone (PVP) and 5 grams Ficoll in 500 ml 20. of water. An exemplary hybridization buffer is one which contains: 5X SSC, 0.5% SDS, 0.02 µg/µl of carrier DNA (calf thymus), 5X PVP/Ficoll, and 2.5% glycerol in a total reaction volume of 25–100 µl.

The presence of glycerol in the hybridization buffer is preferred because the glycerol appears to stabilize the reporter enzyme (with respect to the detrimental effects of exposure to the elevated temperatures preferred for the hybridization reaction). Thus, at concentration below saturation of enzyme concentration, a given amount of reporter enzyme, in the presence of glycerol, provides a higher analytical signal than in the absence of glycerol (due to denaturation of the enzyme). In addition, the presence of glycerol appears to improve the overall hybridization efficiency of the bead-based hybridization system. Thus, for a given amount of target nucleic acid, a greater amount of reporter enzyme becomes part of the sandwich complex, which results in a stronger analytical signal from the same amount of target, compared to a hybridization reaction carried out in the absence of glycerol.

Optionally, prior to the actual hybridization of detection oligonucleotide with the target nucleic acid and/or the simultaneous hybridization of detection oligonucleotide/target nucleic acid/solid support-bound capture oligonucleotide, the solid support-bound capture oligonucleotide can first be subjected to prehybridization conditions suitable to reduce non-specific binding of DNA to the solid support-bound capture oligonucleotide.

Once the sandwich oligonucleotide complex has been formed (either by the simultaneous contacting of detection oligonucleotide/target nucleic acid/solid support-bound capture oligonucleotide, or by the stepwise contacting of target nucleic acid with detection oligonucleotide, followed by contacting of the resulting hybrid with solid support-bound capture oligonucleotide), the resulting complex is washed under conditions suitable to remove substantially all non-specifically bound detection oligonucleotide and extraneous nucleic acid sequences. Preferably, the washing of the sandwich oligonucleotide complex is carried out by contacting said complex at a temperature in the range of about 25°–50° C. with a buffer containing in the range of about 0.1–2.0X SSC and 0–0.1% SDS. Presently most preferred wash conditions include a temperature of about 25° C. with a buffer containing about 0.1X SSC and 0.1% SDS.

After washing, the sandwich complex is ready to be contacted with substrate. Such contacting is carried out under conditions of time and temperature suitable to allow the reporter enzyme to convert substrate into a directly or indirectly detectable product. Reacting of sandwich complex with substrate is typically carried out by maintaining the combination at a temperature in the range of about 25°–37° C. for a time in the range of about 0.1 up to 6 hours. Such contacting produces a signal which can be analyzed by colorimetric, fluorescent, potentiometric, or chemiluminescent means. Preferred substrates are those which are convertible by said reporter enzyme to produce a product which is detectable by chemiluminescent means.

The following examples are included for illustrative purposes only and are not intended to limit the scope of the invention.

EXAMPLES

The capture and detection oligonucleotides used in the following examples have the following nucleotide sequences:

| Sequence designation: | Sequence (5'-3') |
| --- | --- |
| 86-272 (SEQ ID NO 1) | TCTAATTACTACCTCTTCTTCTGCTAGACT |
| 88-297 (SEQ ID NO 2) | TGGCCTAATTCCATGTGTACATTGTACTGT |
| 86-273 (SEQ ID NO 3) | AGTCTAGCAGAAGAAGAGGTAGTAATTAGA |
| 90-673 (SEQ ID NO 4) | AGAAGAGGTAGTAATTAGATCTGCCAATTT |

-continued

| Sequence designation: | Sequence (5'-3') |
|---|---|
| 86-275 (SEQ ID NO 5) | CACAGACAATGCTAAAACCATAATAGTACA |
| 90-422 (SEQ ID NO 6) | AATTAGGCCAGTAGTATCAACTCAACTGCT |
| 90-675 (SEQ ID NO 7) | CATGGAATTAGGCCAGTAGTATCAACTCAACTGCT |

EXAMPLE 1

Synthesis of oligonucleotides.

Detection oligonucleotides 86-272, 90-422, and 90-675 were synthesized on an Applied Biosystems 380A DNA synthesizer using β-cyanoethyl phosphoramidite chemistry and purified by the procedure described by Ghosh et al. ((1987) *Nucl. Acids Res.* 15, 5353). The capture oligonucleotides 88-297, 86-273, 90-673, and 86-.275 which contain a 5'-terminal alkylamine group, were synthesized by using the Aminolink2 reagent (Applied Biosystems, Inc., Foster City, Calif.) in the last coupling step of the automated synthesis. Following the ammonia deprotection step and concentration to dryness, the pellet was taken up in 0.1M triethylammonium acetate (TEAC), pH 8.5 and purified by reverse phase chromatography (CS, 1×25 cm) using a gradient of 7–25% acetonitrile in 0.1M TEAC, pH 6.8. The purified oligonucleotides were stored in 0.2M HEPES, pH 7.7 at −20° C., and were >90% pure when analyzed by 15% denaturing polyacrylamide gel electrophoresis.

EXAMPLE 2

Preparation of the detection oligonucleotide-alkaline phosphatase conjugates (86-272-AP, 90-422-AP, 90-675-AP).

Detection oligonucleotides, 86-272-AP, 90-422-AP, and 90-675-AP, which include calf intestine alkaline phosphatase covalently attached to the oligonucleotide via a thioether linkage, were prepared according to the procedure of Ghosh et al. ((1990) *Bioconjugate Chemistry*, 1, 71). Prior to use, the detection oligonucleotide was diluted in dilution buffer (50 mM NaCl, 10 mM $MgCl_2$, 0.1% gelatin, 0.1M Tris, pH 7.5), such that 12.5 µl of the solution delivered 10–100 fmol of probe for the hybridization reaction.

EXAMPLE 3

Preparation of the polystyrene supported capture oligonucleotides=88-297, 86-273, 90-673, 86-27S.

Prior to the coupling reaction, 1 ml of 10% w/v suspension of 0,807 micron polystyrene CML beads (Seradyn, Indianapolis, Ind.) was filtered using 0.45 µm pore size nylon-66 filter membranes (Rainin, Woburn, Mass.) and washed with 3×10 ml deionized water. The beads were then resuspended in 2 ml of 0.1M imidazole, pH 6.00. Each capture oligonucleotide (6 nmol) was precipitated from storage buffer using LiCl/ethanol, and then redissolved in 1 ml of 0.1M imidazole, pH 6.00. Each oligonucleotide solution was then added to 1 ml of the beads, prepared as described above, with a solution of 125 mg 1-ethyl-3-(dimethylaminopropyl)-carbodiimide in 0.1M imidazole. The reaction mixture was gently agitated in a rotary wheel for 16 hours, after which the beads were filtered, washed successively with 3×10 ml deionized water; 10 ml of 0.3M KCl; 10 ml of water; and finally with 10 ml of 1X SSC, 0.5% SDS. Each sample of beads which contained either oligonucleotide 88-297, 86-273, 90-673, or 86-275 was then resuspended in 2 ml of 1X SSC and stored at 4° C.

EXAMPLE 4

Simultaneous BBSH assays using a oomplementary HIV-1 envelope region RNA transcript as target, and non-complementary HIV-I pollenerase region transcript as negative control.

Presiliconized eppendorf tubes (Denville Scientific Inc., Denville, N.J.) used for the assay were washed with 70% ethanol, and then dried at 55°–60° C. for 30 minutes. Polystyrene-supported capture oligonucleotide [88-297] (50 µg) beads were treated with prehybridization reaction buffer (SX SSC, 5X PVP/Ficoll, 0.5% SDS, 0.02 µg/µl calf thymus DNA) for 20 minutes at 50° C. The beads were then pelleted by centrifugation for 5 minutes at 14,000 rpm.

Twenty-five µl of 2X hybridization buffer (10X SSC, 10X PVP/Ficoll, 1% SDS, 0.04 µg/µl calf thymus DNA, 5% glycerol), 12.5 µl of target or negative control RNA solution in 10 mM Tris, 1 mM EDTA, pH 8.1 (containing the requisite amount of nucleic acid), and 10 fmol of 86-272 detection oligonucleotide in 12.5 µl of dilution buffer were added to the beads and vortexed. The hybridization reaction was allowed to proceed for 1 hour at 50° C. 50 µl of wash solution (0.1X SSC, 0.1% SDS) was added, the mixture was allowed to stand for 3 minutes, centrifuged for 5 minutes, and the supernatant removed. The beads were washed twice with 50 µl of wash solution before addition of the chemiluminescent substrate.

EXAMPLE 5

Two Step BBSH procedure for the detection of target nucleic acid.

Target nucleic acid and 10 fmol of 86-272 detection oligonucleotide were incubated for 30 minutes at 50° C. in 50 µl 1X hybridization buffer. The mixture was quantitatively transferred to an eppendorf tube containing a pelleted form of 50 µg of polystyrene-supported capture oligonucleotide [88-297], then the mixture was vortexed and kept at 50° C. for an additional half hour. After addition of 50 µl of wash solution, the procedure was identical to the final stages of the simultaneous BBSH assay described in Example 4.

EXAMPLE 6

Chemiluminescent detection of a BBSH complex.

200 µl of Lumi-Phos™ 530 (Lumigen Inc., Detroit, Mich.) was added to pelleted beads from a BBSH reaction and gently vortexed. The alkaline phosphatase-catalyzed dephosphorylation of the dioxetane substrate was allowed to occur for 1 hour at 25° C., and in the dark. The mixture was then transferred to a cuvette and the chemiluminescent signal was measured with a Monolight 2010 Luminometer (Advanced Luminescence Laboratory, San Diego, Calif.).

EXAMPLE 7

Simultaneous BBSH followed by chemiluminescent detection using TILISACRYL™ supported oligonucleotide.

A 50 mg suspension of TRISACRYL™-supported detection oligonucleotide [88-297] (see International Application No. PCT/US90/00089) in 10 mM Tris, 0.02% sodium azide, 1 mM EDTA, pH 8.1, was introduced into a fritted microcolumn (Isolab, Inc., Akron, Ohio) and washed two times with 1 ml of diethyl pyrocarbonate (DEPC) treated water. The beads were then hybridized with target nucleic acid and 10 fmol of 86-272 detection oligonucleotide in a total volume of 60 µl of 5X SSC, 5% dextran sulfate, 0.1% SDS, 0.1% gelatin for i hour at 42° C., with constant agitation. The beads were washed with 6×1 ml 2X SSC at 42° C. Lumi-Phos™ 530 (200 µl) was added, and the enzymatic reaction was allowed to proceed for 1 hour at 25° C. in the dark, and with constant agitation of the beads. The mixture was then filtered, and the filtrate was transferred to a cuvette for measuring the chemiluminescent signal with the luminometer.

EXAMPLE 8

Calibration assay for the detection oligonucleotide [86-72] alkaline phosphatase conjugate (86-272-AP).

Presiliconized eppendorf tubes (Denville Scientific Inc., Denville, N.J.) used for the calibration assay were washed with 70% ethanol, and then dried at 55°–60° C. for 30 minutes. Serial dilutions of 86-272-AP detection oligonucleotide conjugate (86-272-AP) were incubated in 50 µl of 1x hybridization buffer (5x SSC, 5x PVP/Ficoll, 0.05% SDS, 0.02 µg/µl calf thymus DNA, 2.5% glycerol), for 1 hour at 50° C. The mixture was then diluted 1:100 in diethyl pyrocarbonate (DEPC) treated water, and 50 µl aliquots (delivering amounts ranging from $10^{-16}$ to $10^{-19}$ moles of the conjugate) were transferred to cuvettes containing 200 µl of LumiPhos™ 530. The alkaline phosphatase-catalyzed dephosphorylation of the dioxetane substrate was allowed to occur in the dark for 1 hour at 25° C. The chemiluminescent signal was measured with Monolight 2010 luminometer (Advanced Luminescence Laboratory, San Diego, Calif.). The data were subjected to linear regression analysis to generate a standard curve, unique to the detection oligonucleotide, which was then used to correlate the chemiluminescent signal to the amount of alkaline phosphatase-conjugated detection oligonucleotide present. Calibration data is set forth in Table 1.

TABLE 1

| CORRELATION OF ALKALINE PHOSPHATASE CONJUGATED PROBE CONCENTRATION TO RELATIVE LIGHT UNITS[1] | | | |
|---|---|---|---|
| 86-272-AP Probe (moles) | 42° C. Signal[2] | 50° C. Signal[2] | 50° C. + 2.5% glycerol Signal[2] |
| $1 \times 10^{-16}$ | 258832 | 169186 | 256380 |
| $1 \times 10^{-17}$ | 28262 | 17234 | 29830 |
| $1 \times 10^{-18}$ | 2808 | 1813 | 3724 |
| $1 \times 10^{-19}$ | 258 | 200 | 408 |

[1]The data presented is the average of triplicate runs; the substrate bakground has been subtracted from the data.
[2]The signal is presented in relative light units These data provide a smooth, linear calibration curve over the entire range tested. Increasing the incubation temperature from 42° C. to 50° C. resulted in a 34% decrease in the signal generated by the conjugate probe. The addition of 2.5% glycerol to the hybridization solution increased the signal by 34%, thus regaining the enzymatic activity lost by the increase in temperature.

EXAMPLE 9

Effect of hybridization conditions on BBSH with alkaline phosphatase-conjugated probes and polystyrene supported capture oligonucleotide.

The bead-based sandwich hybridization protocol described in Example 4 was repeated under a variety of conditions to determine the effect of temperature and/or glycerol on the efficiency of the hybridization reaction. Results are summarized in Table 2.

TABLE 2

| EFFECT OF HYBRIDIZATION CONDITIONS ON SANDWICH HYBRIDIZATIONS WITH AP-CONJUGATED PROBES AND POLYSTYRENE SUPPORT[1] | | | | | | |
|---|---|---|---|---|---|---|
| | 42° C. | | 50° C. | | 50° C. + Glycerol | |
| $32_p$ labeled Transcript (fmol)[3] | Signal[2] | BBSH efficiency | Signal[2] | BBSH efficiency | Signal[2] | BBSH efficiency |
| $5.0 \times 10^{-15}$ | 400695.00 | 3.38 | 885963.00 | 11.15 | Over range[4] | Over range |
| $1.0 \times 10^{-15}$ | 63924.00 | 2.47 | 201511.00 | 13.05 | 690826.00 | 27.00 |
| $4.5 \times 10^{-16}$ | 26339.00 | 2.58 | ND[5] | ND | ND | ND |
| $1.0 \times 10^{-16}$ | ND | ND | 24273.00 | 17.25 | 70264.00 | 29.70 |
| $5.0 \times 10^{-17}$ | ND | ND | ND | ND | 36609.00 | 31.50 |
| $2.0 \times 10^{-17}$ | ND | ND | ND | ND | 14548.00 | 35.15 |

[1]The data presented is the average of triplicate runs; the substrate background has been subtracted from the data. 86-272-AP is the detection oligonucleotide(based on the Ratner sequence 6620–6591); 88-297 is the capture oligonucleotide based on the Ratner sequence(6560–6531).
[2]The signal is presented in relative light units.
[3]The target used is a $^{32}$P-labeled 218 base HIV-1 envelope region RNA transcript defining 6617–6480 region of the Ratner sequence. It was generated from a T-7 RNA polymerase transcription reaction of a T-7 promoter-containing PCR product, using $^{32}$P-α-CTP for incorporation. Quantitation of the target was obtained on the basis of the radioactivity incorporated in the RNA transcript and correlating it to the specific activity of $^{32}$P-α-CTP in the transcription reaction. The primers used in the PCR reaction have the Ratner sequences (6449–6480, and 6617–6661, and include the T-7 promoter sequence at the 5' end).
[4]The signal generated was above the dynamic range of the instrument.
[5]Not determined.

The results set forth in Table 2 demonstrate an increase of both signal and BBSH efficiency upon raising the temperature from 42° C. to 50° C. The efficiency of hybridization was calculated by correlating the signal with the calibration curves for the conjugate (see Table 1). The increase in signal when hybridization is carried out at 50° C. in the presence of glycerol appears to be the result of stabilization of the enzyme, and an improvement in hybridization efficiency in the presence of glycerol.

EXAMPLE 10

Evaluation of various hybridization buffer compositions for use with polystyrene-supported capture oligonucleotides.

A series of hybridization reactions, using 86-273 capture beads and the 90-422 detection probe, were carried out to evaluate the effect of various hybridization buffer components on the invention hybridization reaction. The basic buffer system used is designated 1X HYB, and contains 5X SSC, 0.02µg/µl calf thymus DNA, 2.5% gelatin ±5 x PVP/Ficoll, and ±0.5% SDS. Hybridization results at 50° C. for several modifications of the 1X HYB buffer are summarized in Table 3.

The results set forth in Table 3 demonstrated that PVP/Ficoll is optional and may be omitted from the hybridization solution. The results also indicate that SDS is highly effective for eliminating non-specific interactions between the conjugated probe and the beads.

TABLE 3

| | Signal | | |
|---|---|---|---|
| Buffer | Complementary Target[1] | Non-complementary Target[2] | Signal-Background |
| 1X HYB | 125,266 | 3,322 | 37.7 |
| -SDS | 258,689 | 116,047 | 2.2 |
| -PVP/Ficoll | 176,759 | 2,694 | 43.7 |
| -SDS, PVP/Ficoll | 246,307 | 128,057 | 1.9 |

[1]The complementary target is an env transcript from a 3SR amplification reaction.
[2]The non-complementary target is a pol transcript from a 3SR amplification reaction.

EXAMPLE 11

Comparison of the sensitivities of BBHS assays using chemiluminescence and $^{32}$P detection systems.

The sensitivities of bead-based sandwich hybridizations using alkaline phosphatase-conjugated probe and $^{32}$P-labeled probe with polystyrene-supported capture oligonucleotide directed to a HIV-1 sense RNA transcript were compared at a hybridization temperature of 50° C. according to the procedure set forth in Example 4. Results are summarized in Table 4.

Comparison of the signal to background ratios, set forth in Table 4, demonstrates that the level of sensitivity of the assay using the non-isotopic conjugate is comparable to that of the assay using a $^{32}$P-labeled probe.

TABLE 4

BBSH CHEMILUMINESCENCE vs. $^{32}$P-BASED DETECTION SYSTEMS[1]

| 3SR Target(uL)[2] | 86-272-AP[3] Signal-Background | 86-272-$^{32}$P[4] Signal-Background |
|---|---|---|
| 1 × 10$^{-3}$ | Over Range[5] | 1082 |
| 5 × 10$^{-4}$ | 473 | 310 |
| 1 × 10$^{-4}$ | 139 | 136 |
| 1 × 10$^{-5}$ | 14 | 12 |

[1]The data presented is the average of duplicate runs, and the background signal was generated by using a target that is non-complementary to the detection and capture oligonucleotides. The background target used is an RNA transcript from a 3SR amplification reaction of the HIV-1 polymerase region using the primers defined by nucleotides 2188–2218 and 2919–2888 (and having the T-7 promoter sequence at its 5' end) of the Ratner sequence (see Ratner et al. (1985) Nature, 31:277–284).
[2]The target used is an RNA transcript from a 3SR amplification reaction of the HIV-1 envelope region using the primers defined by nucleotides 6450–6479 and 6661–6632 (and having the T-7 promoter sequence at its 5' end) of the Ratner sequence.
[3]The signal is presented in relative light units; substrate background has been subtracted from the data.
[4]The signal is presented in counts per minute; instrument background has been subtracted from the data.
[5]The signal generated was above the dynamic range of the instrument.

The BBSH assay was conducted as described in Example 4, but using 86-273 polystyrene beads and the 90-422-AP detection probe to detect various amounts of antisense SR-amplified HIV-1 env region product generated by the primers 88-211/88-347(SEQ ID NO 8/SEQ ID NO 9). A parallel set of experiments was conducted in which $^{32}$P-labeled 90-422 oligonucleotide was used as the detection probe under the same hybridization conditions. The results demonstrated that enzyme-based chemiluminescence detection was 10-fold more sensitive than $^{32}$P detection. The sensitivities of BBSH assays using chemiluminescent and $^{32}$P detection systems to detect the sense 3SR-amplified HIV-1 env region product with 86-297 polystyrene beads and 88-272 detection probes was observed to be equivalent.

TABLE 5

CAPTURE EFFICIENCIES FOR TRISACRYL ™ AND POLYSTYRENE BEADS IN BOTH DIRECT AND SANDWICH HYBRIDIZATION FORMATS

| Complementary | % Capture | | | |
|---|---|---|---|---|
| | Direct[1] | | Sandwich[2] | |
| Target Size | TRISACRYL ™[3] | Polystyrene[4] | TRISACRL ™[3] | Polystyrene[4] |
| 30 nt | 90.0 | 81.6 | — | — |
| 218 nt | 69.3 | 36.1 | 26.3 | 10.0 |
| 474 nt | 60.5 | 32.1 | 43.6 | 25.4 |
| 809 nt | 59.2 | 21.0 | 43.0 | 14.1 |

TABLE 5-continued

CAPTURE EFFICIENCIES FOR TRISACRYL ™ AND POLYSTYRENE BEADS IN BOTH DIRECT AND SANDWICH HYBRIDIZATION FORMATS
% Capture

| Complementary | Direct[1] | | Sandwich[2] | |
|---|---|---|---|---|
| Target Size | TRISACRYL ™[3] | Polystyrene[4] | TRISACRL ™[3] | Polystyrene[4] |

[1]The env target sequences were $^{32}$P-labeled for direct capture experiments. The 30 base synthetic oligonucleotide target was labelled at its 5'-end using T-4 poly nucleotide kinase and $^{32}$P-α-ATP. The remaining target molecules are RNA transcripts of a PCR product containing a T-7 RNA polymerase promoter; $^{32}$P-α-CTP was used for incorporation in the transcription reaction. Quantitation was based on label incorporated in transcript, which was measured by UV absorbance and correlation of the concentration of the specific activity of the labelled CTP.
[2]Cold target transcripts were used in the sandwich hybridization reactions in which the detection oligonucleotide (30 bases long) is 5'-labelled with $^{32}$P radioisotope.
[3]Trisacryl beads (25 mg) were not prehybridized. The beads were hybridized in the column with 125 μl 5 × SSPE, 0.1% SDS, 10% dextran sulfate containing 10 fm of target and for the sandwich hybridization 50 fm labelled detection oligonucleotide for 2 hours at 42° C.
[4]Polystyrene beads (50 μg with immobilized capture oligonucleotide) also were prehybridized and hybridized in 50 μl 5 × SSPE, 0.1% polyvinyl pyrrolidone/ficoll, and 20 ng/μl calf thymus DNA. Direct capture was for 1 hour at 60° C. The sandwich hybridization of the polystyrene beads was in 125 μl of buffer containing 10 fm of target and 50 fm of labelled detection oligonucleotide. Sandwich hybridization was for 2 hours at 50° C.

EXAMPLE 12

Comparison of capture efficiency of TRIBACRYL™ and Polystyrene-supported oligonucleotides with $^{32}$P-labelled detection oligonucleotide.

The capture efficiencies of TRISACRYL™-supported capture oligonucleotide (as described in International Application No. PCT/US90/00089) and polystyrene-supported capture oligonucleotide were compared in both direct capture and sandwich hybridization formats, using a 32P-labelled detection oligonucleotide.

The results, which are are summarized in Table 5, demonstrated that Trisacryl has a much higher capture efficiency with 32P-labelled detection oligonucleotide than the polystyrene-supported capture oligonucleotides.

EXAMPLE 13

Comparison of sensitivity of direct capture systems with Trisacryl and polystyrene-based capture oligonucleotides and alkaline phosphataseconjugate oligonucleotides.

The sensitivity of Trisacryl capture oligonucleotides/alkaline phosphatase conjugate oligonucleotides in direct capture format was compared with the sensitivity of polystyrene capture oligonucleotides/alkaline phosphatase conjugate oligonucleotides in direct capture format.

The results, which are summarized in Table 6, showed that polystyrene-supported capture oligonucleotides provide a comparable level of sensitivity to that observed with Trisacryl-supported capture oligonucleotides when employed in a direct capture format with alkaline phosphatase conjugate oligonucleotide.

TABLE 6

COMPARISON OF TRISACRYL AND POLYSTYRENE SOLID SUPPORT PERFORMANCE IN DIRECT CAPTURE OF ALKALINE PHOSPHATASE CONJUGATE OLIGONUCLEOTIDES

| Detection | Signal (relative light units)[1] | |
|---|---|---|
| Probe (mol)[2] | Trisacryl[3] | Polystyrene[3] |
| $1 \times 10^{-14}$ | 1,183,475 | 821,518 |
| $1 \times 10^{-15}$ | 172,424 | 108,778 |
| $1 \times 10^{-16}$ | 20,999 | 11,032 |
| $1 \times 10^{-17}$ | 2,011 | 1,157 |

[1]The data presented is the average of duplicate runs; substrate background has been subtracted from the data.
[2]86-272-AP is the detection oligonucleotide, which is complementary to the capture oligonucleotide, and is based on the Ratner sequence 6620–6591. The protocol for direct capture for polystyrene and trisacryl supports is a modification of the bead-based sandwich hybridization procedure. Here the detection oligonucleotide (86-272-AP) is the target, and is captured by its complementary oligonucleotide which has been immobilized on the solid supports.
[3]86-273 is the capture oligonucleotide based on the Ratner sequence 6591–6620.

EXAMPLE 14

Comparison of sensitivity of sandwich hybridization format with Trisacryl and Polystyrene-based capture oligonucleotides and alkaline phosphatase conjugate oligonucleotides.

The sensitivity of Trisacryl capture oligonucleotides/alkaline phosphatase conjugate oligonucleotides in sandwich hybridization format was compared with the sensitivity of polystyrene capture oligonucleotides/alkaline phosphatase conjugate oligonucleotides in sandwich hybridization format. Results are summarized in Table 7.

The results demonstrated that polystyrene-supported capture oligonucleotides, when employed in a sandwich hybridization format with alkaline phosphatase conjugate oligonucleotides, provide an enhanced level of sensitivity compared to that observed with Trisacryl-supported capture oligonucleotides.

TABLE 7

COMPARISON OF TRISACRYL AND POLYSTYRENE SOLID SUPPORT PERFORMANCE IN BEAD BASED SANDWICH HYBRIDIZATIONS OF ALKALINE PHOSPHATASE CONJUGATE OLIGONUCLEOTIDES

| Transcript | Signal (relative light units)[1] | |
|---|---|---|
| (moles)[2] | Trisacryl[3] | Polystyrene[3] |
| $1 \times 10^{-14}$ | 197,040 | Over Range[4] |
| $1 \times 10^{-15}$ | 20,035 | 690,826 |
| $1 \times 10^{-16}$ | −651 | 70,264 |
| $2 \times 10^{-17}$ | ND[5] | 14,548 |
| $1 \times 10^{-17}$ | −268 | ND |

[1]The data presented is the average of duplicate runs; substrate background has been subtracted from the data.
[2]The target used is a $^{32}$P-labeled 218 base HIV-1 envelope region RNA transcript defining 6661 to 6450 region of the Ratner sequence. It was generated from a T-7 RNA polymerase transcription reaction of a T-7 promoter-containing PCR product, using $^{32}$P-α-CTP for incorporation. Quantitation of the target was obtained on the basis of the radioactivity incorporated in the RNA transcript and correlating it to the specific activity of $^{32}$P-α-CTP in the transcription reaction. The primers used in the PCR reaction have the Ratner sequences 6450–6479 and 6661–6632 and include the T-7 promoter sequence at their 5' ends.
[3]86-272-AP is the detection oligonucleotide (based on the Ratner sequence 6620–6591); while 88-297 is the capture oligonucleotide (based on the Ratner sequence 6560–6531).
[4]The signal generated was above the dynamic range of the instrument.
[5]ND signifies the data was not determined.

EXAMPLE 15

Effect of polystyrene beads on chemiluminescent detection of sandwich hybridization.

This example considers the effect of polystyrene beads on the detectable chemiluminescent signal. The effect of the presence of polystyrene beads on the chemiluminescent signal obtained upon reaction of substrate with the sandwich complex obtained from polystyrene-supported capture oligonucleotide and alkaline phosphatase-conjugated detection oligonucleotide was investigated. The chemiluminescence of the product was measured both in the presence and in the absence of the polystyrene bound sandwich complex. This was done by either reading the signal of the bead suspension in LumiPhos™ 53D solution, or by centrifuging the suspension and transferring the product-containing supernatant to cuvettes for measurement of the signal. Results are summarized in Table 8.

The data presented in Table 8 indicate that the beads do not appear to interfere with the ability to detect the signal. The apparent increase in signal in the presence of the beads results from the continuation of the reaction between the enzyme and substrate. The signal/background ratio is essentially the same whether the measurement is carried out in the presence or absence of the beads.

EXAMPLE 16

Effect of time on the BBSH assay.

The optimal time for hybridization of 90-422-AP conjugate detection probe to 3SR-amplified HIV-1 RNA env region target RNA at 50° C. in optimized buffer (5X SSC, 0.5% SDS, 0.02 μg/μl calf thymus DNA, 2.5% glycerol) was investigated. Calibration curves generated by plotting CL signal versus moles of 90-422-AP probe after incubation in hybridization buffer without target nucleic acid for various time periods indicated that there was a 10% decrease in enzymatic activity when the incubation time was increased from 60 minutes to 120 minutes and a 40% loss at 150 minutes (data not shown). Table 9 shows that the maximum chemiluminescent signal was observed when the hybridization period, for the 90-422-AP:target-RNA complex, was between 60 and 90 minutes. The signal/negative control ratio was not significantly enhanced by increasing the time of hybridization beyond 60 minutes.

TABLE 8

EFFECT OF POLYSTYRENE BEADS ON DETECTION OF LUMINESCENCE

| | Signal (relative light units (RLUs))1 | |
|---|---|---|
| $^{32}$P-Transcript (1.0 fmole) | with beads[4] | without beads[5] |
| env[2] | 791147 | 698494 |
| pol[3] | 3358 | 3074 |
| Signal-Background | 235 | 227 |

[1]The data presented is the average of duplicate runs; substrate background has been subtracted from the data.
[2]Target is a $^{32}$P labeled env transcript.
[3] $^{32}$P-labeled pol transcript was used to determine the background.
[4]The enzyme continues to react with the substrate when measuring in the presence of the sandwich complex.
[5]The enzyme stops reacting with the substrate when measuring in the absence of the sandwich complex.

TABLE 9

| Time (min) | Signal-Background (RLUs) × 10$^{-3}$ |
|---|---|
| 30 | 95 |
| 60 | 175 |
| 90 | 175 |
| 120 | 165 |
| 150 | 135 |

EXAMPLE 17

Influence of conjugate probe concentration on BBSH sensitivity.

A constant amount of antisense HIV-1 env region RNA target (~2.5 fmole) was assayed with the 86-273 oligonucleotide supported on polystyrene beads and 90-422-AP detection probe, wherein the amount of 90-422-AP detection probe was increased from 10 to 100 fmoles. The results set forth in Table 10 show the chemiluminescent signal increases with increasing amounts of detection probe up to approximately 50 fmoles, after which the signal remains constant.

TABLE 10

| fmoles 90-422-AP Probe | Signal-Background (RLUs) × 10$^{-3}$ |
|---|---|
| 10 | 40 |
| 20 | 85 |
| 30 | 120 |
| 40 | 140 |
| 50 | 235 |
| 60 | 260 |
| 70 | 260 |
| 80 | 230 |
| 90 | 240 |

EXAMPLE 18

Influence of the length of the alkyl spacer in the conjugate on the sensitivity of the BBHH assay.

The maleimide-thiol coupling reaction was used to synthesize two sets of alkaline phosphatase-oligonucleotide conjugates, in which the enzyme moiety was separated from the nucleic acid with ethylene and hexylene spacers, respectively. The 86-272-AP conjugates are complementary to the sense strand of env HIV-1 RNA, and the 90-422-AP conjugates are complementary to antisense env region HIV-1 RNA. As shown in Table 11, the 86-272-AP that includes a six-carbon spacer between the oligonucleotide and the enzyme, as probe for the detection of the sense strand, generated a two-fold larger chemiluminescent signal than the 86-272-AP that includes a two-carbon spacer. A similar result was observed using the 90-422-AP antisense detection probes. A three-fold increase in signal was obtained upon increasing the length of the spacer from 2 to 6 carbons.

TABLE 11

| Detection Probe | CL Signal (RLUs) $\times 10^{-3}$ | |
| --- | --- | --- |
| Conjugate | 2 Carbon | 6 Carbon |
| 86-272-AP | 60 | 120 |
| 90-422-AP | 12 | 40 |

EXAMPLE 19

Effect of detection probe length on the sensitivity of the BBSH assay.

Detection probes 90-422-AP and 90-675-AP were used in combination with oligonucleotides 86-273, 90-673 or 86-275 (SEQ. ID Nos. 3–5, respectively) bound to polystyrene capture beads to detect a 350 base length antisense env region HIV-1 RNA target in the BBSH assays. Conjugate probe 90-675-AP is identical in sequence to 90-422-AP, but has an additional five bases complementary to the target sequence appended at the 5' end. The sequence of 90-673 (SEQ ID No. 3) oligonucleotide is shifted 11 bases downstream from 86-273 (SEQ ID No. 4), and the 86sequence is 41 bases downstream from 86-273.

The results of the assays are set forth in Table 12.

For all bead combinations, the 90-675-AP probe generates a larger signal than the 90-422-AP conjugate. Extending the spatial distance between sequences included in the detection and capture probes, as with the 86-275 polystyrene beads, was detrimental for hybridization.

TABLE 12

| | CL Signal (RLUs) $\times 10^{-3}$ | |
| --- | --- | --- |
| Capture Oligbeads ™ | 90-422-AP | 90-675-AP |
| 86-273 (SEQ ID NO. 3) | 20 | 31 |
| 90-673 (SEQ ID NO. 4) | 19 | 30 |
| 86-275 (SEQ ID NO. 5) | 4 | 6 |

EXAMPLE 20

Correlation of CL signal with the amount of 3SR amplified antisense-HIV RNA target.

Linear regression analysis of a plot of chemiluminescent signal as a function of 3SR-amplified HIV-1 env region antisense RNA product, obtained from BBSH assays at various target concentrations using the 90-422-AP detection probe and 86-273 polystyrene capture beads, demonstrated a direct correlation between the signal observed for target amounts ranging between $10^{-17}$ moles to $10^{-14}$ moles. A deviation from linearity observed in the calibration curve for higher target concentrations arose at concentrations of target in excess of the 90-422-AP conjugate detection probe used in the assay.

EXAMPLE 21

Use of the BBBH assay to detect HIV-1-infected GEM cells.

Serial dilutions of HIV-1-infected CEN cells in a background of $10^6$ uninfected peripheral blood mononuclear cells were lysed using guanidinium isothiocyanate, and the HIV-I RNA was isolated by affinity purification using Trisacryl OligoBeads™. The RNA was then amplified using the 3SR reaction and the products were detected by BBSH using 86-273 polystyrene capture beads and the 90-422-AP conjugate detection probe. The amplified products were quantitated by correlation of the chemiluminescent signal to a calibration curve generated with known amounts of HIV-1 env region RNA.

The results indicated that the conjugate 90-422-AP probe detects one HIV-1 infected CEM cell in a background of $10^6$ PBMC cells (Peripheral Blood Mononucleocytes) when the BBSH assay is prefaced with a 3SR amplification reaction.

Since modifications will be apparent to those of skill in the art, it is intended that this invention be limited only by the scope of the appended claims.

That which is claimed is:

1. A method for detecting a single-stranded target nucleic acid, comprising:
   (a) hybridizing said target nucleic acid with a detection oligonucleotide to form a target nucleic acid-detection oligonucleotide complex,
   wherein said detection oligonucleotide has a reporter enzyme covalently bound thereto and forms a stable hybrid with a first portion of the target nucleic acid;
   (b) hybridizing said complex with a polystyrene support-bound capture oligonucleotide to form a sandwich complex comprising the capture oligonucleotide, the target nucleic acid, and the,
   wherein the capture oligonucleotide is covalently bound to the polystyrene support and forms a stable hybrid with a second portion of said target nucleic acid, and said first and second portions do not overlap, and
   wherein the hybridization reactions of steps (a) and (b) are conducted simultaneously or sequentially;
   (c) washing said polystyrene support-bound, capture oligonucleotide-target nucleic acid-detection oligonucleotide sandwich complex under conditions sufficient to remove substantially all unhybridized detection oligonucleotide therefrom; and
   (d) detecting said sandwich complexes, whereby the concentration of said target nucleic acid is measured.

2. The method of claim 1, wherein said detection is effected by reacting said sandwich complex with a suitable substrate under conditions such that the reporter enzyme promotes the conversion of said substrate to produce a detectable signal; and measuring said signal and thereby determining the concentration of said target nucleic acid.

3. The method of claim 2, wherein said signal is detected by color metric, fluorescent, potentiometric, or chemiluminescent means and/or wherein said substrate is converted to a product which is detected by chemiluminescent means.

4. The method of claim 3, wherein said substrate is selected from the group consisting of dioxetane derivatized substrates for alkaline phosphatase, β-galactosidase, aryl esterase and sulfatase.

5. The method of claim 2, wherein the reacting of sandwich complex with substrate is carried out at a temperature in the range of about 25°–37° C. for a time in the range of about 0.1 up to 5 hours.

6. The method of claim 1, wherein said target nucleic acid includes a sufficient number of nucleotides to form a stable hybrid with both said capture and detection oligonucleotides and is less than about 2000 nucleotides in length.

7. The method of claim 1, wherein said target nucleic acid is all or a detectable portion of a human immunodeficiency virus (HIV) genome.

8. The method of claim 1, wherein prior to the hybridization of step (a) said target nucleic acid is amplified.

9. The method of claim 8, wherein said amplification is effected by 3SR amplification, TAS amplification or PCR amplification.

10. The method of claim 1, wherein said polystyrene support is in the form of beads having a particle-size in the range of about 0.1 up to 10 microns, and wherein said. polystyrene beads contain a sufficient number of functional groups for covalent attachment of a concentration of at least 0.1 nmol per gram of polystyrene polymer of the capture oligonucleotide to the polystyrene polymer.

11. The method of claim 10, wherein said functional groups are selected from the group consisting of carboxyl groups, amine groups, aldehyde groups, hydrazine groups, epoxide groups, bromoacetyl groups, maleimide groups and thiol groups.

12. The method of claim 11, wherein the concentration of capture oligonucleotide, per gram of polystyrene polymer, falls in the range of about 1 up to 300 nmol/g.

13. The method of claim 1, wherein the capture oligonucleotide and/or detection oligonucleotide include at least about 20 nucleotides.

14. The method of claim 1, wherein the reporter enzyme is selected from the group consisting of alkaline phosphatase, horseradish peroxidase, β-galactosidase, aryl esterase, urease, and sulfatase.

15. The method of claim 1, wherein said hybridization of target nucleic acid with detection oligonucleotide is carried out at a temperature in the range of about 25°–55° C. for a time in the range of about 0,1 up to 6 hours.

16. The method of claim 15, wherein said hybridization is carried out in a buffer that contains a sufficient amount of glycerol to reduce the amount of denaturation of the reporter molecule and a concentration of salt in which hybrids that Include more than about 1% mismatched base pairs are unstable.

17. The method of claim 16, wherein the hybridization of target nucleic acid-detection oligonucleotide complex with capture oligonucleotide is carried out at a temperature in the range of about 25° up to 55° C. for about 0.1 up to 6 hours.

18. The method of claim 16, wherein said washing is effected by contacting said complex at a temperature in the range of about 25°–50° C. with a buffer containing in the range of about 0.1–2.0 X SSC and 0–0.1% SDS.

19. The method of claim 1, wherein the washing of the sandwich oligonucleotide complex is carried out under conditions suitable to remove substantially all non-specifically bound detection oligonucleotide and extraneous nucleic acids.

20. The method of claim 1, wherein the hybridization reactions of steps (a) and (b) are conducted sequentially.

21. A kit for the detection of target nucleic acids, comprising, in a container suitable for packaging, reagents for a bead-based sandwich hybridization assay for the detection of single-stranded, target nucleic acids, wherein said reagents include:

(a) a detection oligonucleotide that has a reporter enzyme covalently bound thereto and that includes a sufficient number of nucleotides that are complementary to a first portion of the target nucleic acid to form a stable hybrid;

(b) a capture oligonucleotide that is covalently bound to a polystyrene support and that includes a sufficient number of nucleotides that are complementary to a second portion of the target nucleic acid to form a stable hybrid, wherein said first and second portions do not overlap; and (c) a substrate for the reporter enzyme, wherein said substrate is selected from the group of substrates converted by said enzyme into a product that is detectable by chemiluminescent, colorimetric, potentiometric, or fluorescent means.

22. The kit of claim 21, further comprising a container with a composition comprising hybridization buffer containing glycerol.

* * * * *

UNITED STATES PATENT AND TRADEMARK OFFICE
CERTIFICATE OF CORRECTION

PATENT NO. : 5,474,895

DATED : December 12, 1995

INVENTOR(S) : Ishii et al.

It is certified that error appears in the above-indentified patent and that said Letters Patent is hereby corrected as shown below:

column 3, line 17, after "capture", change "oligonucleotides-are" to —oligonucleotides are—;

column 5, line 60, before "or bacterial", change "vital" to —viral—:

column 7, line 20, after "for example,", change "Maniatie" to —Maniatis—;

column 7, line 25, after "IRL Press.", begin a new line with the heading "The bead-based hybridization assay system."

column 7, line 30, between "viruses" and "in blood", change "(HIVe)," to —(HIVs),—;

column 8, line 57, between "Ghosh" and "(1987)", change "etal." to —et al.—;

column 10, line 10, after "using the", change "Aminolink2reagent" to —Aminolink2 reagent—;

column 10, line 26, after "(1987)", change "*Nuleic*" to —*Nucleic*—;

column 11, line 44, after "about: 2-5X", change "SSC,0.1-0.5%" to —SSC, 0.1-0.5%—;

column 11, line 48, between "a" and "PVP/Ficoll", change "10)" to —10X—;

column 11, line 50, between "ml" and "of", delete "20.";

EXAMPLE 1, column 13, line 24, between "chromatography" and "1x25", change "(CS," to —(C8,—;

EXAMPLE 4, column 14, line 11, after "using a", change "oomplementary" to —complementary—;

EXAMPLE 4, column 14, line 13, between "complementary" and "transcript", change "HIV-I pollenerase" to —HIV-1 polymerase—;

EXAMPLE 7, column 14, line 67, between "using" and "supported", change "TILISACRYL™" to —TRISACRYL™—;

EXAMPLE 7, column 15, line 10, between "for" and "hour", change "i" to —1—;

UNITED STATES PATENT AND TRADEMARK OFFICE
CERTIFICATE OF CORRECTION

PATENT NO. : 5,474,895

DATED : December 12, 1995

INVENTOR(S) : Ishii et al.

It is certified that error appears in the above-indentified patent and that said Letters Patent is hereby corrected as shown below:

EXAMPLE 12, column 19, line 25, after "efficiency of", change "TRIBACRYL™" to —TRISACRYL™—;

EXAMPLE 12, column 19, line 32, after "using a", change "32P-" to —$^{32}$P-—;

EXAMPLE 12, column 19, line 36, between "with" and "labelled", change "32P-" to —$^{32}$P-—;

EXAMPLE 13, column 19, line 44, between "alkaline" and "oligonucleotides", change "phosphataseconjugate" to —phosphatase conjugate—;

EXAMPLE 19, column 23, line 42, between "the" and "is", change "86sequence" to —86-275 sequence—;

EXAMPLE 21, column 24, line 30, after "HIV-1-infected", change "GEM" to —CEM—;

EXAMPLE 21, column 24, line 32, between "HIV-1-infected" and "cells", change "CEN" to —CEM—;

UNITED STATES PATENT AND TRADEMARK OFFICE
CERTIFICATE OF CORRECTION

PATENT NO. : 5,474,895

DATED : December 12, 1995

INVENTOR(S) : Ishii et al.

It is certified that error appears in the above-indentified patent and that said Letters Patent is hereby corrected as shown below:

in Claim 3, column 30, line 59, between "by" and "fluorescent,", change "color metric," to —colorimetric—; and in Claim 16, column 32, line 1, before "more", change "Include" to —include—.

Signed and Sealed this

Thirtieth Day of April, 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
    ( A ) NAME/KEY: misc_feature
    ( B ) LOCATION: 1..30
    ( D ) OTHER INFORMATION: /note="86-272 OLIGONUCLEOTIDE"

( x i ) SEQUENCE DESCRIPTION: SEQ ID NO:1:

TCTAATTACT ACCTCTTCTT CTGCTAGACT      30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..30
        ( D ) OTHER INFORMATION: /note="88-297 OLIGONUCLEOTIDE"

( x i ) SEQUENCE DESCRIPTION: SEQ ID NO:2:

TGGCCTAATT CCATGTGTAC ATTGTACTGT      30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..30
        ( D ) OTHER INFORMATION: /note="86-273 OLIGONUCLEOTIDE"

( x i ) SEQUENCE DESCRIPTION: SEQ ID NO:3:

AGTCTAGCAG AAGAAGAGGT AGTAATTAGA      30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..30
        ( D ) OTHER INFORMATION: /note="90-673 OLIGONUCLEOTIDE"

( x i ) SEQUENCE DESCRIPTION: SEQ ID NO:4:

AGAAGAGGTA GTAATTAGAT CTGCCAATTT      30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (ii) MOLECULE TYPE: DNA (genomic)

(ix) FEATURE:
    (A) NAME/KEY: misc_feature
    (B) LOCATION: 1..30
    (D) OTHER INFORMATION: /note="86-275 OLIGONUCLEOTIDE"

(xi) SEQUENCE DESCRIPTION: SEQ ID NO:5:

CACAGACAAT GCTAAAACCA TAATAGTACA                                    30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /note="90-422 OLIGONUCLEOTIDE"

(xi) SEQUENCE DESCRIPTION: SEQ ID NO:6:

AATTAGGCCA GTAGTATCAA CTCAACTGCT                                    30

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /note="90-675 OLIGONUCLEOTIDE"

(xi) SEQUENCE DESCRIPTION: SEQ ID NO:7:

CATGGAATTA GGCCAGTAGT ATCAACTCAA CTGCT                              35

(2) INFORMATION FOR SEQ ID NO:8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..57
        (D) OTHER INFORMATION: /note="88-211 OLIGONUCLEOTIDE"

(xi) SEQUENCE DESCRIPTION: SEQ ID NO:8:

AATTTAATAC GACTCACTAT AGGGATCTAT TGTGCCCCGG CTGGTTTTGC GATTCTA      57

(2) INFORMATION FOR SEQ ID NO:9:

(i) SEQUENCE CHARACTERISTICS:
        (A) LENGTH: 56 base pairs
        (B) TYPE: nucleic acid
        (C) STRANDEDNESS: single ( D ) TOPOLOGY: linear ( i i ) MOLECULE TYPE: DNA (genomic)

( i x ) FEATURE:
    ( A ) NAME/KEY: misc_feature
    ( B ) LOCATION: 1..56
    ( D ) OTHER INFORMATION: /note="88-347 OLIGONUCLEOTIDE"

( x i ) SEQUENCE DESCRIPTION: SEQ ID NO:9:

AATTTAATAC GACTCACTAT AGGGATGTAC TATTATGGTT TTAGCATTGT CTGTGA      5 6

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..31
        ( D ) OTHER INFORMATION: /note="89-255 OLIGONUCLEOTIDE"

( x i ) SEQUENCE DESCRIPTION: SEQ ID NO:10:

TTATTGTGCC CCGGCTGGTT TTGCGATTCT A      3 1

( 2 ) INFORMATION FOR SEQ ID NO:11:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..55
        ( D ) OTHER INFORMATION: /note="90-374 OLIGONUCLEOTIDE"

( x i ) SEQUENCE DESCRIPTION: SEQ ID NO:11:

AATTTAATAC GACTCACTAT AGGGATTTTT CTTGTATTGT TGTTGGGTCT TGTAC      5 5